United States Patent
Freeman

(10) Patent No.: US 8,805,491 B2
(45) Date of Patent: Aug. 12, 2014

(54) MICROPERFUSIVE ELECTRICAL STIMULATION

(75) Inventor: Gary A. Freeman, Newton Center, MA (US)

(73) Assignee: ZOLL Medical Corporation, Chelmsford, MA (US)

(*) Notice: Subject to any disclaimer, the term of this patent is extended or adjusted under 35 U.S.C. 154(b) by 0 days.

(21) Appl. No.: 10/868,395

(22) Filed: Jun. 15, 2004

(65) Prior Publication Data

US 2005/0234515 A1  Oct. 20, 2005

Related U.S. Application Data

(60) Provisional application No. 60/564,160, filed on Apr. 20, 2004.

(51) Int. Cl.
*A61N 1/362* (2006.01)
*A61N 1/39* (2006.01)

(52) U.S. Cl.
CPC .................................. *A61N 1/3906* (2013.01)
USPC ................................................. 607/3; 607/5

(58) Field of Classification Search
USPC .............................................. 607/2–5, 9, 11
See application file for complete search history.

(56) References Cited

U.S. PATENT DOCUMENTS

| | | | |
|---|---|---|---|
| 3,460,542 A | 8/1969 | Gemmer | |
| 3,547,108 A | 12/1970 | Sieffert | |
| 3,716,059 A | 2/1973 | Welborn et al. | |
| 4,088,138 A | 5/1978 | Diack et al. | |
| 4,349,030 A | 9/1982 | Belgard et al. | |
| 4,904,472 A * | 2/1990 | Belardinelli et al. | 514/263.1 |
| 4,928,690 A | 5/1990 | Heilman et al. | |
| 4,980,379 A | 12/1990 | Belardinelli et al. | |
| 5,188,106 A * | 2/1993 | Nappholz et al. | 607/24 |
| 5,205,284 A | 4/1993 | Freeman | |
| 5,314,448 A * | 5/1994 | Kroll et al. | 607/5 |
| 5,405,362 A * | 4/1995 | Kramer et al. | 607/5 |
| 5,462,524 A * | 10/1995 | Powell et al. | 601/52 |
| 5,588,422 A * | 12/1996 | Lurie et al. | 128/200.24 |
| 5,733,869 A * | 3/1998 | Burhop et al. | 514/6 |
| 5,827,893 A * | 10/1998 | Lurie et al. | 514/653 |
| 6,090,056 A * | 7/2000 | Bystrom et al. | 601/41 |
| 6,096,063 A | 8/2000 | Lopin et al. | |

(Continued)

FOREIGN PATENT DOCUMENTS

| | | |
|---|---|---|
| WO | WO 97/15351 | 5/1997 |
| WO | WO 97/25098 | 7/1997 |

(Continued)

OTHER PUBLICATIONS

AHA Guidelines 2000 for CPR and Emergency Cardiovascular Care, Circulation, 2000, 102(8), Supplement, I-22 through I-171.

(Continued)

Primary Examiner — Carl H Layno
Assistant Examiner — Jessica Anthony
(74) Attorney, Agent, or Firm — Fish & Richardson P.C.

(57) ABSTRACT

A method of treating a patient in cardiac arrest (e.g., in fibrillation, electrochemical dissociation, or asystole), the method comprising delivering an agent for enhancement of cardiac function to the coronary arteries of the patient; and microperfusing the patient's cardiac tissue by electromagnetically stimulating the cardiac tissue at an energy level below a threshold sufficient to defibrillate the heart.

10 Claims, 10 Drawing Sheets

(56) References Cited

U.S. PATENT DOCUMENTS

| | | | |
|---|---|---|---|
| 6,149,670 A * | 11/2000 | Worthen et al. | 607/3 |
| 6,236,887 B1 * | 5/2001 | Ben-Haim et al. | 607/3 |
| 6,253,108 B1 | 6/2001 | Rosborough et al. | |
| 6,259,949 B1 | 7/2001 | Rosborough et al. | |
| 6,263,241 B1 | 7/2001 | Rosborough et al. | |
| 6,556,865 B2 | 4/2003 | Walcott et al. | |
| 2002/0183682 A1 * | 12/2002 | Darvish et al. | 604/20 |
| 2002/0193833 A1 | 12/2002 | Dimmer et al. | |
| 2003/0083698 A1 | 5/2003 | Whitehurst et al. | |
| 2004/0186546 A1 * | 9/2004 | Mandrusov et al. | 607/122 |
| 2004/0230140 A1 * | 11/2004 | Steen | 601/41 |
| 2005/0096570 A1 * | 5/2005 | Palazzolo et al. | 601/44 |

FOREIGN PATENT DOCUMENTS

| | | |
|---|---|---|
| WO | WO 00/21609 | 4/2000 |
| WO | WO 00/042914 | 7/2000 |
| WO | WO 01/28609 | 4/2001 |
| WO | WO 01/34088 | 5/2001 |
| WO | WO 01/39761 | 6/2001 |
| WO | WO 02/060528 | 8/2002 |

OTHER PUBLICATIONS

US 5,584,866, 12/1996, Kroll et al. (withdrawn)

* cited by examiner

FIGURE 10

Deliver at least one of, or a combination of more than one of, substances with uncharged molecules. The substances chosen from: aspartate, oxaloacetate, glutamate, or 2-oxoglutarate to the patient.

Electromagnetically stimulate the cardiac tissue to microperfuse the cardiac tissue with the uncharged molecules.

MICROPERFUSIVE ELECTRICAL STIMULATION

CROSS-REFERENCE TO RELATED APPLICATIONS

This application claims priority to U.S. Provisional Application Ser. No. 60/564,160, filed on Apr. 20, 2004.

TECHNICAL FIELD

This invention relates to the treatment of cardiac arrest, and in particular to the electromagnetic stimulation of the heart for the treatment of cardiac arrest.

BACKGROUND

Cardiac Arrest, or Sudden Death, is a descriptor for a diverse collection of physiological abnormalities with a common cardiac etiology, wherein the patient typically presents with the symptoms of pulselessness, apnea and unconsciousness. Cardiac arrest is widespread, with an estimated 300,000 victims annually in the U.S. alone and a similar estimate of additional victims worldwide. Early defibrillation is the major factor in sudden cardiac arrest survival. There are, in fact, very few cases of cardiac arrest victims saved which were not treated with defibrillation. There are many different classes of abnormal electrocardiographic (ECG) rhythms, some of which are treatable with defibrillation and some of which are not. The standard terminology for this is "shockable" and "non-shockable" ECG rhythms, respectively. Non-shockable ECG rhythms are further classified into hemodynamically stable and hemodynamically unstable rhythms. Hemodynamically unstable rhythms are those which are incapable of supporting a patient's survival with adequate blood flow (non-viable). For example, a normal sinus rhythm is considered non-shockable and is hemodynamically stable (viable). Some common ECG rhythms encountered during cardiac arrest that are both non-shockable and hemodynamically unstable are: bradycardia, idioventricular rhythms, pulseless electrical activity (PEA) and asystole. Bradycardias, during which the heart beats too slowly, are non-shockable and also possibly non-viable. If the patient is unconscious during bradycardia, it can be helpful to perform chest compressions until pacing becomes available. Idioventricular rhythms, in which the electrical activity that initiates myocardial contraction occurs in the ventricles but not the atria, can also be non-shockable and non-viable (usually, electrical patterns begin in the atria). Idioventricular rhythms typically result in slow heart rhythms of 30 or 40 beats per minute, often causing the patient to lose consciousness. The slow heart rhythm occurs because the ventricles ordinarily respond to the activity of the atria, but when the atria stop their electrical activity, a slower, backup rhythm occurs in the ventricles. Pulseless Electrical Activity (PEA), the result of electromechanical dissociation (EMD), in which there is the presence of rhythmic electrical activity in the heart but the absence of myocardial contractility, is non-shockable and non-viable and would require chest compressions as a first response. Asystole, in which there is neither electrical nor mechanical activity in the heart, cannot be successfully treated with defibrillation, as is also the case for the other non-shockable, non-viable rhythms. Pacing is recommended for asystole, and there are other treatment modalities that an advanced life support team can perform to assist such patients, e.g. intubation and drugs. The primary examples of shockable rhythms that can be successfully treated with defibrillation are ventricular fibrillation, ventricular tachycardia, and ventricular flutter.

Normally, electrochemical activity within a human heart causes the organ's muscle fibers to contract and relax in a synchronized manner. This synchronized action of the heart's musculature results in the effective pumping of blood from the ventricles to the body's vital organs. In the case of ventricular fibrillation (VF), however, abnormal electrical activity within the heart causes the individual muscle fibers to contract in an unsynchronized and chaotic way. As a result of this loss of synchronization, the heart loses its ability to effectively pump blood. Defibrillators produce a large current pulse that disrupts the chaotic electrical activity of the heart associated with ventricular fibrillation and provides the heart's electrochemical system with the opportunity to re-synchronize itself. Once organized electrical activity is restored, synchronized muscle contractions usually follow, leading to the restoration of effective cardiac pumping.

First described in humans in 1956, transthoracic defibrillation has become the primary therapy for cardiac arrest, ventricular tachycardia (VT), and atrial fibrillation (AF). Monophasic waveforms dominated until 1996, when the first biphasic waveform became available for clinical use. Attempts have also been made to use multiple electrode systems to improve defibrillation efficacy. While biphasic waveforms and multiple-electrode systems have shown improved efficacy relative to monophasic defibrillation, there is still significant room for improvement: shock success rate for ventricular fibrillation (VF) remains less than 70% even with the most recent biphasic technology. In these cases, shock success was defined to be conversion of a shockable rhythm into a non-shockable rhythm, including those non-shockable rhythms which are also non-viable. Actual survival-to-hospital-discharge rates remain an abysmal ten percent or less. Survival rates from cardiac arrest remain as low as 1-3% in major U.S. cities, including those with extensive, advanced prehospital medical care infrastructures.

The initial rhythm following a defibrillation shock is rarely a perfusing, viable rhythm and almost always is asystole or PEA, neither of which is treatable with defibrillation. In addition, recent studies have shown rates of ventricular fibrillation (VF) and shockable ventricular tachycardias (VT) to be unexpectedly low. A recent report from Goteborg, Sweden shows VF to be present in only 39% of cases. Similar results have been reported from Seattle and Ontario, Canada. Ornato et al in a study of hospital cardiac arrest found only 25% of patients presented with a shockable rhythm (VF/VT); 66% presented with non-shockable rhythms asystole and PEA. There is even retrospective clinical data that indicates that the rates of non-shockable PEA and asystole are increasing in cardiac arrest victims.

Given that neither of these rhythms is treatable with defibrillation, there is a justifiable clinical concern that the treatment protocols currently recommended by expert groups such as the American Heart Association are inadequate. A recent publication by Ewy proposed that certain elements of the present AHA guidelines [AHA Guidelines 2000 for CPR and Emergency Cardiovascular Care, Circulation 2000; 102 (8), Supplement] regarding Basic and Advanced Life Support (BLS, ALS) field protocols may be contributing factors in the poor survival rates for cardiac arrest. The term basic life support (BLS) refers to maintaining airway patency and supporting breathing and circulation without the use of equipment other than a protective shield. BLS comprises the elements: initial assessment; airway maintenance; expired air ventilation (rescue breathing); and chest compression. When all three (airway breathing, circulation) are combined the term cardiopulmonary resuscitation (CPR) is used. Personnel trained in ALS will also deliver drugs, as well as such advanced techniques as intubation, administration of intravenous fluids and suturing in addition to BLS techniques. In the currently recommended treatment protocols, BLS personnel should perform CPR on cardiac arrest victims whose rhythm is either PEA or asystole; ALS personnel have the additional treatments available of intubation, intravenous administration and the drugs epinephrine and atropine. None of these ALS techniques, however, have been particularly effective in the treatment of either PEA or asystole. Assuming a rate of PEA and asystole of 66% in cardiac arrest victims, 400,000 of the 600,000 total worldwide cardiac arrest victims would present in physiological states for which there was no effective treatment for their condition, which has a 0% survival rate, it should be noted, if left untreated.

A new protocol, coined "CPR First", is being considered which reemphasizes the importance of perfusion. It is currently proposed as follows: for patients with a known (witnessed) collapse time of less than 4 minutes, perform the present field protocol; for patients with prolonged (greater than 4 minutes) or unknown collapse time, (1) immediately begin uninterrupted chest compressions prior to a defibrillation shock (various lengths of time for compression are being considered, starting with 90 seconds or greater), (2) only apply one defibrillation shock (e.g., a biphasic waveform) at the end of the first chest compression cycle, and (3) followed immediately by 200 uninterrupted chest compressions prior to a cardiac rhythm analysis by an automated external defibrillator (AED) or by the rescuer trained in the analysis of ECG rhythms, providing a defibrillation shock as necessary (repeat steps 1-3 for as long as deemed necessary). As long as the patient remains unconscious, the rescuer can alternate between use of the defibrillator (for analyzing the electrical rhythm and possibly applying a shock) and performing cardiopulmonary resuscitation (CPR). CPR generally involves a repeating pattern of five or fifteen chest compressions followed by providing the victim with a number of breaths. CPR is generally ineffective against abnormal rhythms, but it does keeps some level of oxygenated blood flow going to the patient's vital organs until an advanced life support team arrives.

The treatment window for cardiac arrest is very narrow. Long term survival rates from the time of victim collapse decrease at a roughly exponential rate with a time constant of roughly 2 minutes. Thus, just two minutes of delay in treatment using the currently recommended treatment protocols result in a long term survival rate of 30-35%. After 15 minutes, the long term survival rates are below 5%. While the response times of emergency medical systems have improved significantly over the last quarter century to the point that average times from emergency call to arrival at the victim is typically 9 minutes or less, bystander delays in making the emergency call typically add 2-3 minutes to the total arrest time, for a total of 11-12 minutes. In addition, the bystander making the emergency call may not even have witnessed the cardiac arrest, which may have occurred at some point in the past. Unwitnessed arrest accounts for at least half of all cardiac arrests. Cardiac arrest downtimes are only reported for witnessed arrests; it has been estimated, however, that if unwitnessed arrests were to be included, the average downtime for all victims would exceed 15 minutes. At the time of initial collapse, the ECGs of nearly all cardiac arrest victims are shockable rhythms such as VF or VT; after 15 minutes, however, the ECG rhythms of most cardiac arrest victims have degenerated into the non-shockable rhythms of PEA or asystole.

Excitation-Contraction (E-C) coupling describes the process by which the electrical signal, initiated in the S-A node in normal hearts, is converted to a mechanical contraction in the myocardial cells. Excitation-contraction coupling begins when an action potential depolarizes the plasma membrane surrounding the myocardial cell, which generates an electrical signal by allowing ions to flow through ion-selective channels in the plasma membrane. Two cations, sodium and calcium, carry the inward currents that depolarize the heart, while the cation potassium carries the outward current that repolarizes the heart and is the primary determinant of the heart's resting potential. Excitation of the cells of the atria and ventricles begins when opening of the sodium channels generates an inward (depolarizing) sodium current. The resulting change in membrane potential opens calcium channels that trigger calcium release from the sarcoplasmic reticulum.

Calcium ions, by carrying signals generated at the cell surface to a variety of intracellular proteins and organelles, can be viewed as the most important of the intracellular messengers. Myocardial cells use calcium as the essential final step in excitation-contraction coupling, the process by which depolarization at the cell surface initiates the interactions between the contractile proteins that cause the walls of the heart to develop tension and contract.

Calcium binding to troponin-C triggers interactions between actin and myosin by reversing an inhibitory effect of the regulatory proteins. This response begins with a series of cooperative interactions between calcium-bound troponin-C and other proteins of the thin filaments: actin, tropomyosin, troponin-I, and troponin-T. Calcium binding to troponin-C weakens the bond linking troponin-I to actin, causing a structural rearrangement of the regulatory proteins that shifts the tropomyosin deeper into the grooves between the strands of actin. This rearrangement exposes active sites on actin for interaction with the myosin cross bridges.

The ultrastructure of the myocardial cell is shown in FIG. 1. The sarcomere is the functional unit of the contractile apparatus. The sarcomere is defined as the region between the successive Z-lines and contains two half-I-bands and one A-band. Contractile proteins are arranged in a regular array of thick and thin filaments (seen in cross section at the left). The A-band represents the region of the sarcomere occupied by the thick filaments into which the thin filaments extend from either side. The I-band is the region of the sarcomere occupied only by the thin filaments; these extend toward the center of the sarcomere from the Z-lines, which bisect each I-band. The sacroplasmic reticulum, a membrane network that surrounds the contractile proteins, consists of the sarcotubular network at the center of the sarcomere and the cisternae, which abut the t-tubules and the sarcolemma, so that the lumen of the t-tubules carries the extracellular space toward the center of the myocardial cell.

At rest, active transport processes (mainly the sodium-potassium pump) maintain electrochemical gradients across the sarcolemmal membrane. Consequently, a resting membrane potential is established with the cell interior being negative relative to the extracellular space. Depolarization of the cardiac sarcolemmal membrane occurs largely due to opening of sodium channels, which results in an influx of sodium and a rapid rise in membrane potential from negative to positive values. This change in membrane potential is ultimately translated into an increase in intracellular cytosolic calcium, binding of calcium to the contractile protein complex in the myofibrils, and cell shortening (contraction).

Relaxation occurs as the resting sarcolemmal membrane potential is reestablished, intracellular cytosolic calcium decreases, and calcium dissociates from the contractile protein complex.

FIG. 2, shows the primary calcium fluxes of both the E-C coupling and relaxation. The thickness of each arrow represents the magnitude of the calcium flux, and their vertical orientation describe whether or not the flux is generated by passive or active transport: downwardly-directed arrows represent passive flux while upwardly-directed arrows represent energy-dependent active calcium transport. Most of the calcium that enters the cell from the extracellular fluid via the L-type calcium channels (arrow A) triggers calcium release from the sacroplasmic reticulum; only a small portion directly activates the contractile proteins (arrow A1). Calcium is actively transported back into the extracellular fluid by the plasma membrane calcium pump ATPase (arrow B1) and the Na/Ca exchanger (arrow B2). The sodium that enters the cell in exchange for calcium (dashed line) is pumped out of the cytosol by the sodium pump. The channels providing inward-directed calcium flux are: 1) L-type channels, located in the transverse tubular system, in close proximity to the calcium release channels of the sarcoplasmic reticulum; and 2) T-type channels not concentrated in t-tubules but can be found on the plasma membrane of the myocardial cells. The channels providing outward-directed calcium flux are: 1) plasma membrane calcium pump (PMCA), a low volume pump; and 2) the Na/Ca exchanger.

Calcium entry via L-type calcium channels is among the most important determinants of myocardial contractility. This calcium entry serves two functions: it triggers the opening of the intracellular calcium release channels in the sarcoplasmic reticulum and provides most of the activator calcium that binds to troponin, and it fills the internal calcium stores. Only a small amount binds directly to the contractile proteins of the adult heart, which depends mainly on the intracellular calcium cycle. B-adrenergic agonists are known to increase L-type channel flow, while both calcium and beta-channel blockers are known to inhibit calcium flux through the L-type calcium channels.

The Na/Ca exchanger transports three sodium ions in one direction across the membrane for a single calcium ion that moves in the opposite direction, which means that the Na/Ca exchange is electrogenic. Therefore, calcium efflux, which relaxes the heart, is favored during diastole, whereas calcium influx increases contractility during systole.

Two calcium fluxes are regulated by the sacroplasmic reticulum: calcium efflux from the sarcolemmal cisternae via calcium release channels (arrow C) and calcium uptake into the sarcotubular network by the sarco(endo)plasmic reticulum calcium pump ATPase (arrow D). Calcium diffuses within the sacroplasmic reticulum from the sarcotubular network to the sarcolemmal cisternae (arrow G), where it is stored in a complex with calsequestrin and other calcium-binding proteins. Calcium binding to (arrow E) and dissociation from (arrow F) high-affinity calcium binding sites of troponin-C activate and inhibit the interactions of the contractile proteins. Calcium movements in and out of the mitochondria (arrow H) buffer cytosolic calcium concentration. The extracellular calcium cycle consists of arrows A, B1, and B2, whereas the intracellular cycle involves arrows C, D, E, F, and G.

In addition, the relaxation cycle of diastole is regulated primarily by calcium uptake by the sarco(endo)plasmic reticulum calcium(SERCA) pump (arrow D) and calcium uptake by the mitochondria (arrow H), which together provide the function of normalizing and stabilizing cytosolic calcium levels.

The most distinctive phase of the cardiac action potential is the plateau phase, generally termed phase 2 (phase 0 is the action potential upstroke, phase 1 is the early depolarization, phase 3 is the repolarization phase, and phase 4 is diastole) generated by counterbalancing ionic fluxes of an inward cardiac current and outward potassium current. The major role of the plateau is to prevent the heart from being reactivated before the ventricles have had time to fill after the preceding systole. It is calcium flux generated by L-type channels that provides the important duration extension of phase 2.

It is well known to those skilled in the art that the sustained energy demands of the heart can be met only by the mechanism of oxidative phosphorylation, which requires that the coronary circulation deliver an uninterrupted supply of the metabolic substrates, notably oxygen. The myocardial ischemia induced by cardiac arrest has a number of important metabolic effects. In addition to the prevention of the delivery of oxygen to the myocardial cells, there is an accumulation of protons (H+) and lactate. The resulting acidosis inhibits glycolysis and adversely affects contractility. Further, phosphate and potassium accumulate which contribute to arrhythmogenesis and reduced contractility. Cytosolic calcium concentrations increase during ischemia due to the reduced cytosolic calcium uptake into the sarcotubular network by the SERCA pump, caused by lowered ATP levels within the ischemic milieu. During the early stages of ischemia, approximately <20 minutes, the Na/Ca exchanger gradually drains the calcium from the cytosol. While cytosolic concentrations of calcium may be higher due to the reduced function on the SERCA pump, there is a net depletion of calcium within the cell during ischemia that needs to be ameliorated before heart function can be returned to normal. EC coupling fails under this condition resulting in PEA and asystole. Global myocardial ischemia induced during cardiac arrest has effects related to lack of oxygen, but also effects from the prevention of the removal of metabolites which accumulate in the ischemic heart such as protons (H+), phosphate, potassium and lactate. Acidosis from H+ and lactate inhibits glycolysis and reduces both contractility and relaxation. Potassium contributes to the genesis of arrhythmias while phosphate decreases contractility.

Prior art in defibrillation has focused on the cessation of fibrillation such as U.S. Pat. Nos. 3,460,542, 3,547,108, 3,716,059, 4,088,138 and 4,928,690. Transcutaneous pacing of the heart for treatment of bradycardias as well as asystole and electromechanical dissociation can be found in such prior art as U.S. Pat. No. 4,349,030. U.S. Pat. No. 5,584,866 teaches a method for achieving cardiac output during fibrillation by increasing the amplitude of the pacing stimulus. U.S. Pat. Nos. 5,205,284, 6,253,108 B1, 6,259,949 B1, and 6,263,241 B1 describe the use of higher frequency pulses in the treatment of EMD. U.S. Pat. Nos. 5,314,448 and 6,556,865 B2 both describe the electrical pretreatment of the fibrillating heart in order to improve defibrillation results.

SUMMARY

In a first aspect, the invention features a method of treating a patient in cardiac arrest (e.g., in fibrillation, electrochemical dissociation, or asystole), the method comprising delivering an agent for enhancement of cardiac function to the coronary arteries of the patient; and microperfusing the patient's cardiac tissue by electromagnetically stimulating the cardiac tissue at an energy level below a threshold sufficient to defibrillate the heart.

In preferred implementations, one or more of the following features may be incorporated. The method of delivering the agent may comprise intravenous infusion of the agent and a circulatory enhancement method for delivery of the agent to the coronary arteries. The circulatory enhancement method may comprise manual chest compressions. The circulatory enhancement method may comprise assistance by a chest compression device. The circulatory enhancement method may comprise assistance by a cardiac mechanical pump. The method of delivery may comprise direct injection into the coronary arteries. The agent may comprise a metabolite. The metabolite may comprise at least one of, or a combination of more than one of, aspartate, glucose, NAD+, proglycogen, or 2-oxoglutarate. The agent may comprise a metabolic enhancing agent. The metabolic enhancing agent may comprise at least one of, or a combination of more than one of, epinephrine, insulin, Dobutamine, norepinephrine, catecholamine, or sympathomimetic agent. The electromagnetic stimulation may comprise an internally applied defibrillation pulse. The electromagnetic stimulation may comprise an externally applied defibrillation pulse. The invention may further comprise delivering a defibrillation pulse to the patient's cardiac tissue following the delivering and microperfusing steps. The order in which the steps are performed may be delivering the agent, followed by circulatory enhancement of the agent, followed by microperfusing. The metabolic enhancing agent may comprise the oxidized form of nicotinamide adenine dinucleotide (NAD+). The invention may further comprise delivering calcium. The agent may comprise at least one of the following metabolites: aspartate, glucose, proglycogen, or pyruvate. The delivering step may comprise intravenous delivery. The delivering step may comprise intraosseus delivery. The delivering step may comprise transcutaneous delivery. The invention may further comprise making a determination of whether or not the patient has suffered an asphyxial arrest or an arrest of cardiac origin. If the arrest is determined to be of cardiac origin, cardiac compressions may be performed with larger compression than would be performed if the arrest were not of cardiac origin, and the method may further comprise ventilation. The delivering step may comprise cardiac compression performed by chest compression. The chest compression may comprise using equipment that automatically provides chest compressions. Equipment performing chest compressions may be electrically connected to equipment that provides the electromagnetic stimulation. The equipment that provides electromagnetic stimulation may comprise an external defibrillator and/or pacemaker. The electrical current may comprise a biphasic pulse. The electrical current may comprise a multiphasic pulse. The biphasic pulse may be about 25 to 500 volts in amplitude. The invention may further comprise additional biphasic pulses concatenated into a multiphasic pulse train up to about 1 ms to 100 ms in duration. The biphasic pulse may be about 100 to 200 volts in amplitude. The biphasic pulses may comprise a series of four 10 ms biphasic pulses over a duration of 40 ms. The individual biphasic pulses may be about 500 microseconds (minimum 50, maximum 1000) in duration, with about a 400 microsecond first phase and about a 100 microsecond second phase with a spacing between pulses of about 9.5 ms. The average amplitude of the pulse train may be adjusted by changing the duty cycle of the biphasic pulses, consistent with observation that for shorter duration biphasic pulses, less than approximately 1 ms in duration, the myocardium responds to the average current of the pulse train.

In a second aspect, the invention features a method of stimulating cardiac tissue, the method comprising delivering at least two distinct waveform morphologies to the patient, either interleaved or sequentially, wherein a first waveform is configured to increase the therapeutic effect of a first therapeutic agent on a particular cardiac tissue to which the first agent is directed, and wherein a second waveform is configured to increase the therapeutic effect of a second therapeutic agent on a particular cardiac tissue to which the second agent is directed.

In preferred implementations, one or more of the following features may be incorporated. The first waveform may comprise a series of high frequency pulses (e.g., 50 to 1000 microseconds in duration) and the first therapeutic agent may comprise a metabolic agent (e.g., glucose). The second waveform may comprise a series of low frequency pulses (e.g., 1 to 100 ms in duration) and the second therapeutic agent may comprise ions such as calcium. The two waveforms may comprise a high frequency (e.g., 50 to 1000 microsecond duration) and a pacing pulse. The two waveforms may comprise a high frequency pulse and a biphasic current pulse. The two waveforms may be overlapping. The two pulses may be sequential.

In a third aspect, the invention features a method of treating a patient in cardiac arrest (e.g., in fibrillation, electrochemical dissociation or asystole), the method comprising microperfusing the patient's cardiac tissue by electromagnetically stimulating the cardiac tissue at an energy level below a threshold sufficient to defibrillate the heart, and delivering a pacing pulse and/or a defibrillation pulse to the patient, wherein the microperfusing, pacing, and defibrillation are delivered by varying the duty cycle, shape, and/or rate of delivery of a series of pulses delivered from the energy storage device.

In a fourth aspect, the invention features a method of treating a patient in cardiac arrest (e.g., in fibrillation, electrochemical dissociation, or asystole), the method comprising delivering a pacing pulse to the cardiac tissue; and delivering a defibrillation pulse to the cardiac tissue, wherein the pacing pulse has the same waveform as the defibrillation pulse but with a difference in amplitude.

In a fifth aspect, the invention features a method of treating a patient in cardiac arrest (e.g., in fibrillation, electrochemical dissociation, or asystole), the method comprising delivering at least one of, or a combination of more than one of, aspartate, oxaloacetate, glutamate, or 2-oxoglutarate to the patient; electromagnetically stimulating the cardiac tissue.

In preferred implementations, one or more of the following features may be incorporated. The stimulation may comprise defibrillation stimulation. The stimulation may comprise pacing stimulation. The stimulation may comprise below threshold defibrillation or pacing stimualation. The stimulation may comprise MPES stimulation.

Among the many advantages of the invention (some of which may be achieved only in some of its various aspects and implementations) are that the invention can provide improved efficacies relative to prior art. None of the prior art anticipates the enhancement of circulation at the myocardial cellular level by electromagnetic stimulation as described herein, nor the use of the electromagnetic stimulation to deliver therapeutic agents into the myocardial cytosolic volume.

While survival rates for ventricular fibrillation can be as high as 50% in some emergency medical systems, survival for victims presenting in PEA or asystole is dismal, usually less than 5%. Current estimates of prevalence of PEA and asystole as the presenting rhythm in cardiac arrest is 50%, or 200,000 victims annually worldwide who could be helped with a more effective treatment. Current treatment methods such as the drug atropine or pacing have been shown to have little if any benefit to this class of patients. Neither therapy effectively promotes self-sustaining, organized rhythmicity or contractility of the heart. CPR and chest compressions alone are helpful only for those patients whose myocardial E-C coupling is still viable—a small subset of patients presenting with this condition.

Electrical stimulation of ion and metabolite transfer mechanisms have the additional benefit of a significantly shorter half life than cardiac drugs such as beta or calcium channel blockers or vasopressin. One of the limitations of the use of drugs during a cardiac arrest is that the drugs may be beneficial in achieving resuscitation, but deleterious with the return of spontaneous circulation, e.g. a cardioactive drugs like vasopressin.

Other features and advantages of the invention will be apparent from the drawings, detailed description, and claims.

BRIEF DESCRIPTION OF THE DRAWINGS

FIG. 10 is a block diagram of another implementation of the method of the invention.

DETAILED DESCRIPTION

There are a great many possible implementations of the invention, too many to describe herein. Some possible implementations that are presently preferred are described below. It cannot be emphasized too strongly, however, that these are descriptions of implementations of the invention, and not descriptions of the invention, which is not limited to the detailed implementations described in this section but is described in broader terms in the claims.

It has been discovered by the inventor that, contrary to what has been previously thought, the primary purpose for the transverse tubule (t-tubule) system is not for the transmission of the electrical excitation signal deep into the cell interior, nor is the ion transport in the myocardial T-tubule system accomplished by diffusion. Rather, the primary purpose for the t-tubule system is for ion transport to the cell interior, and the mechanism for that transport is in actuality a chemomechanical pump. It is well known to those skilled in the art that the t-tubule system and the sarcoplasmic reticulum do not develop in mammals until several months after birth. The number of myocardial cells does not increase in mammals subsequent to birth; rather, heart size is increased by enlargement of the individual myocardial cells. During development of newborn cardiac tissue, as the diameter of the cells increase, transcriptional triggers occur which result in t-tubules forming primarily along the Z-lines of cells, L-type calcium channels forming alongside the t-tubules and the sacroplasmic reticulum forming with cisternae adjacent to the t-tubules. The reason for this structural change is because the increasing radii of the myocardial cells and the resulting increase in cell surface area to volume ratio make diffusion-only transport of calcium ions to the cell interior ineffective. Effective cell depolarization can be accomplished by ion transport localized to the sarcolemma, the outer surface of the myocardial cell; such is not the case for activation of the E-C coupling by calcium which requires transport of the calcium to the specific actin-myosin interface undergoing contraction.

Figure 3A:
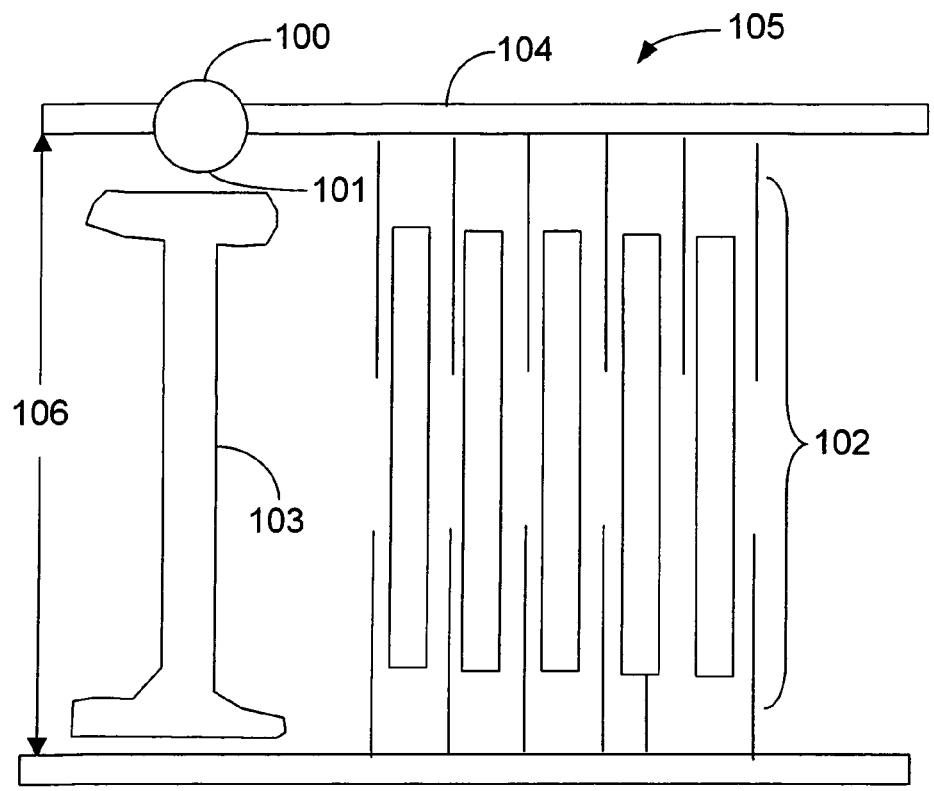
FIG. 3a, 3b are diagrammatic illustrations showing the chemomechanical pumping sequence.
Figure 3B:
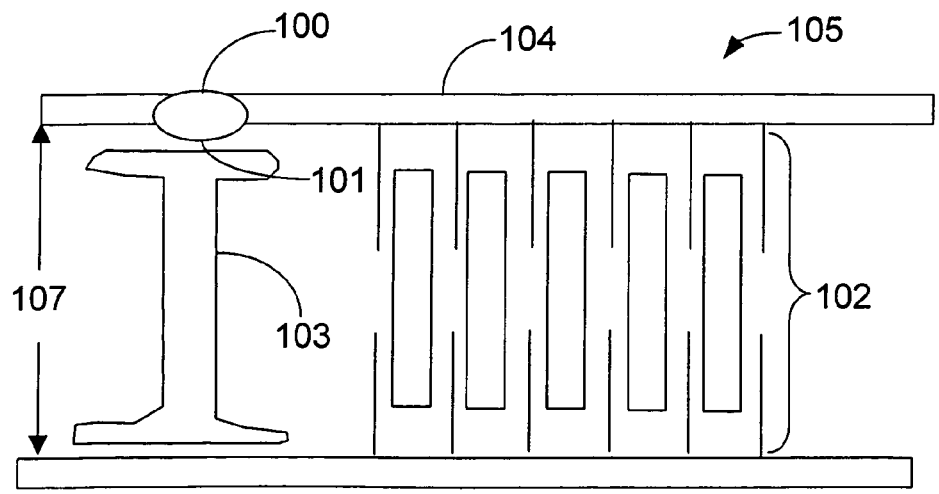

FIGS. 3a and 3b depict the chemomechanical pumping sequence. The t-tubules 100, L-type calcium channels 101, the sarcomere 102 and sacroplasmic reticulum 103 together form a chemomechanical pump system wherein calcium-rich extracellular fluid is pumped into the t-tubules during relaxation and calcium-depleted fluid is pumped out the t-tubules during myocardial contraction. In FIG. 3b, the myocardium is contracted and the sarcomere length, $L_{Ssys}$ 107, is shorter than that during myocardial relaxation phase, $L_{Sdias}$ 106 as shown in FIG. 3a. The reduced sarcomeric length results in an increased cytosolic pressure, forcing compression of the t-tubules 100 located primarily along the Z-line 104, thus reducing t-tubule diameter and causing the ejection of the ion and metabolite-depleted contents of the t-tubule 100 into the extracellular space 105. During diastole, sarcomere length increases, reducing cytosolic pressure, thus increasing t-tubule diameter and causing the injection of the ion and metabolite-rich extrasystolic fluid into the t-tubule. While other channels are located inside the t-tubule such as GLUT4 channels for glucose transmission across the membrane, the primary purpose of the t-tubule is to deliver calcium to the interior of the myocardial cell via the L-type calcium channel 101. L-type channels 101 are voltage-gated by sarcolemmal membrane potential derived from flow of sodium and potassium ions during systole and deliver the calcium at a lower, steadier and more long-lasting rate than other ion channels. L-type calcium current is not used for contraction via activation of the actin-myosin complex. Rather, it activates the calcium induced calcium release (CICR) via the ryanodine receptor (RyR). CICR occurs only from the sarcolemmal cisternae located at the t-tubules. There is thus a significant calcium concentration gradient along the axis of the sarcomere, with the highest concentrations located between the t-tubule and the sarcolemmal cisternae. Calcium travels in the cytosol along the sarcomere, diffusion-driven by the concentration gradient, causing activation of the actin-myosin complex of the sarcomere first in those areas along the Z-line 104 and then progressively toward those locations furthest away from the t-tubule 100 and Z-line 104. This results in a concentrated contraction beginning first around the t-tubules 100, enhancing the ejection of the t-tubule contents. L-type calcium currents continue during much of the contraction, reducing the calcium ion and metabolite concentration in the t-tubule fluid. During diastole, sarcomere length increases, injecting metabolite and calcium-rich extracellular fluid back into the t-tubule, beginning the cycle once again.

In addition to the transfer of calcium and, to a lesser extent, glucose across the t-tubule membrane, there are the better known channels located on the exterior sarcolemmal membrane that transfer the various ions, nutrients and metabolites. This whole system we term microperfusion to differentiate it from the vascular-based circulation carried by the coronary arteries and their branches which we term macroperfusion.

In some implementations, interventions to enhance both macroperfusion and microperfusion either simultaneously or in specific sequences based on the underlying clinical etiology are combined to provide the optimal therapy for the patient.

Some implementations may be used for treating all patients in cardiac arrest of non-traumatic, non-overdose origin. Step one of the treatment procedure is to identify all patients whose cardiac arrest is the result of trauma or overdose. This is easily accomplished by standard clinical methods, after which the patient is treated for the underlying trauma or overdose. Patients are further categorized into those whose cardiac arrest is of cardiac etiology and those for whom the cardiac arrest was the result of asphyxia such as choking, hanging, drowning, etc.

The course of treatment will vary based on the etiology. In some implementations, all treatment courses contain the following three phases: macroperfusion therapy (MPT), microperfusive electrical stimulation (MPES) and circulatory/electrical therapy (CET). MPT generally involves intravenous delivery of therapeutic agents, e.g. a catecholamine such as epinephrine or norepinephrine, a metabolite such as glucose, glycogen, proglycogen or pyruvate, and a constituent ion solution such as potassium ($K^+$) or calcium ($Ca^+$), followed by a period of cardiopulmonary resuscitation (CPR). MPES involves electrical stimulation of the myocardium with the appropriate waveform morphology, frequency components and amplitude such that the various therapeutic agents are delivered to the myocardial sarcolemmal membrane and into the cytosolic space of the myocardial cells either by such mechanisms as the previously-mentioned calcium chemomechanical pump or by more conventional ion transport channels known to those skilled in the art. CET involves such well-known therapies as defibrillation and pacing, and may be sequenced either before or after the MPT and MPES phases. In some suboptimal embodiments, explicit delivery of therapeutic agents may be missing, for instance it may be the case that the therapeutic intent is only to deliver $Ca^+$ to the cytosol, in which case there may be sufficient extracellular calcium present in ischemia for accomplishing this goal utilizing MPES. Also, a patient may be resuscitated prior to CET, in which case there are only the MPT and MPES phases of therapy; there is thus a minimal configuration of the invention with includes only the MPT phase consisting of only CPR and the MPES phase of therapy.

Figure 6:
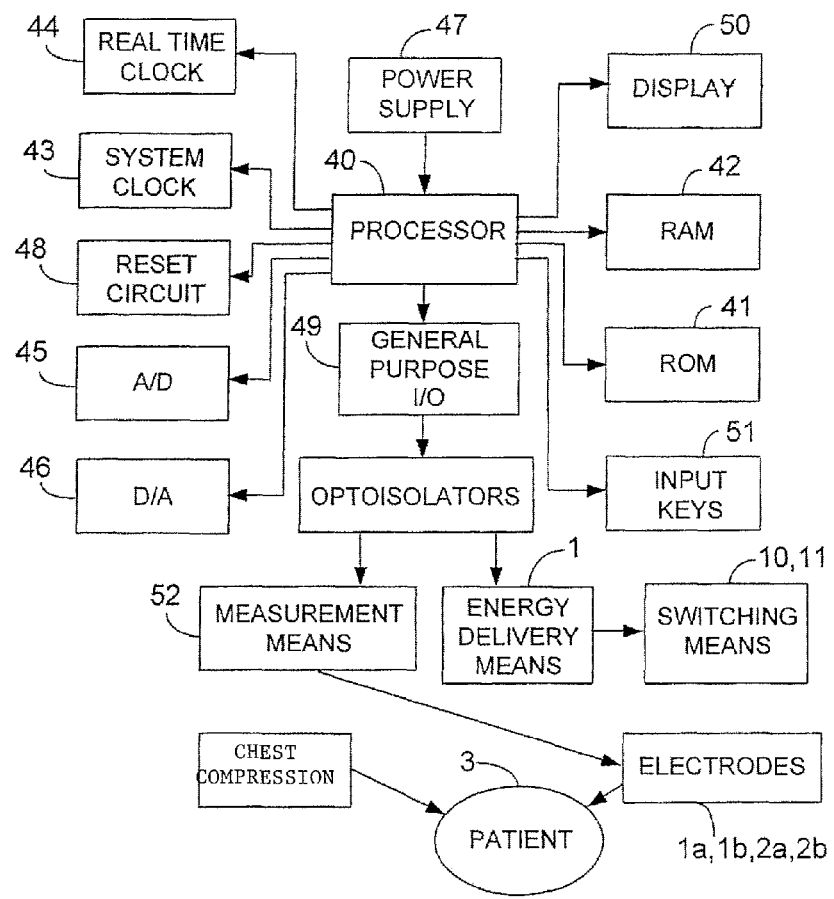
FIG. 6 is a block diagram of an implementation including the circuitry of FIG. 5 combined with apparatus for performing chest compression.

Referring to FIG. 6, one possible implementation has the function of chest compression integrated with that of an external defibrillator/pacemaker such as manufactured by ZOLL Medical (Chelmsford, Mass.). The chest compression function may be provided by devices such as a piston-based system such as that manufactured by Michigan Instruments (Michigan) or a constricting band system such as that manufactured by Revivant Corp. (California). The integration may take the form of physical integration of the defibrillator/pacemaker and the chest compressor into a single device, but alternatively it may be a functional integration of two separate devices by a communication means such as a wireless scheme like Bluetooth or a serial communication interface such as RS232, USB or Ethernet.

When used by advanced cardiac life support personnel (ACLS), the MPT phase includes intravenous or intraosseus delivery of therapeutic agents as well as an initial assessment of whether or not the cardiac arrest was the result of asphyxia. In the case of asphyxial arrest as well as cardiac arrests with a presenting rhythm of asystole or PEA, the patient will receive one minute of chest compressions combined with active ventilations while the therapeutic agents are being prepared in order to alleviate hypercarbia. A combination of norepinephrine (5 mg), epinephrine (1 mg), are then delivered as a bolus intravenously, with an IV infusion of a combination of 25% glucose, 50 IU soluble insulin per liter at an infusion rate of 1 $mL \cdot kg^{-1} \cdot h^{-1}$. The glucose/insulin solution may be included in the initial bolus. Norepinephrine enhances cyclic AMP (cAMP) which, in turn, results in increased glycogenolyis and glucose uptake via the GLUT4 channels, and enhanced calcium uptake by the L-type calcium channels resulting in enhanced contractility. Dobutamine may be substituted for norepinephrine and epinephrine. The patient then receives one more minute of chest compressions.

In one implementation, the amino acid aspartate is delivered as part of an initial intravenous infusion prior to the MPES phase. In another embodiment utilizing aspartate, the aspartate is delivered in an MPT infusion phase, followed by electrical stimulation of the heart utilizing defibrillation or pacing therapy without any intervening MPES phase. The aspartate infusion is preferably a Ringer's solution with the sodium concentration adjusted to account for the additional sodium due to the 20 mmol/L of sodium L-aspartate added to provide the L-aspartate. The infusate may also include the combination of glucose and insulin. Aspartate is particularly effective in increasing ATP production of the myocardium under the ischemic conditions of cardiac arrest by enhancing anaerobic ATP production in glycolysis. Aspartate also has the beneficial effect of a reduction of fumarate in mitochondria thus potentially lower the risk of reperfusion injury after a successful defibrillation. Normally, reduced nicotinamide adenine dinucleotide (NADH) generated from glycolysis is reoxidized to NAD+ by reduction of pyruvate to lactate. Under ischemic conditions, this results in a build-up of lactate in the cytosol which is harmful to the myocardium. This is avoided by aspartate or 2-oxoglutarate. Aspartate is transaminated to oxaloacetate with the resulting amino group transferred to form alanine by way of a reaction involving pyruvate and glutamate. Oxaloacetate is then converted to malate with an oxidation of NADH to create NAD+. Ischemia arrests glycolysis at the glyceraldehyde phosphate dehydrogenase step due to a lack of NAD+. Thus the increased concentrations of NAD+ due to the aspartate will result in significantly enhanced ATP production without the deleterious lactate production usually encountered in anaerobic glycolysis. The malate is then transported across the mitochondrial barrier. During effective CPR or upon successful resuscitation of the patient when oxygenated blood is being delivered to the myocardium, the enhanced levels of malate leads to enhancement of the reduction of fumarate to succinate, coupled with ATP formation in complex 1 of the respiratory chain.

In cases where the presenting rhythm is VF, a defibrillation shock may be delivered prior to the MPT and MPES phases as described in the preceding paragraph. It has been found that substitution of vasopressin for epinephrine in this situation provides better outcomes for the patient.

Following the second one-minute cycle of chest compressions, the catecholamines, ions and metabolites have been delivered via the coronary arteries and their branches into the myocardium. In order to accomplish delivery of the various therapeutic agents into the cytosol, one minute of MPES is delivered.

Figure 4A:
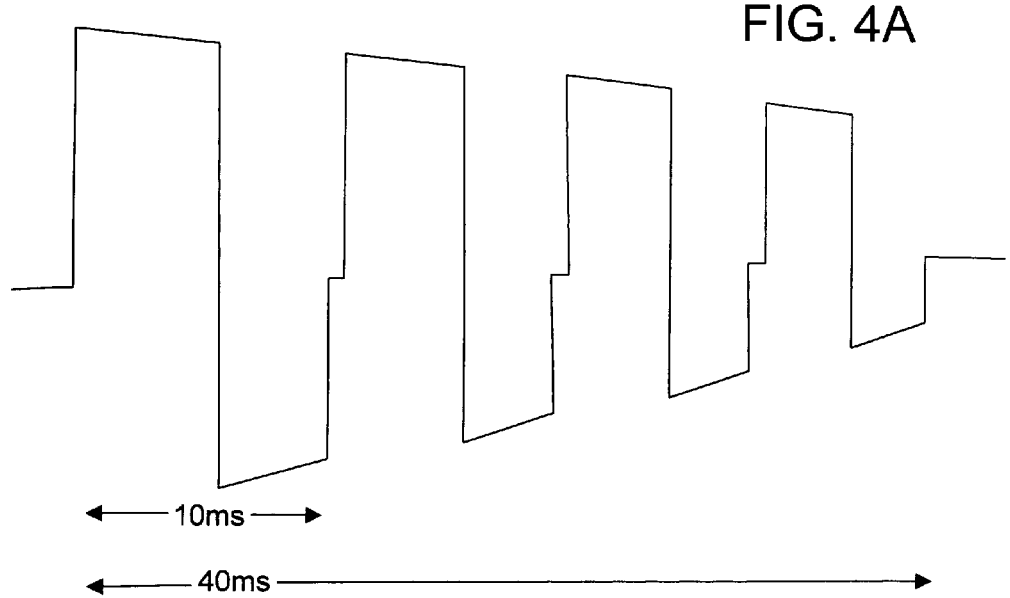
FIG. 4a, 4b are plots of waveforms produced by the implementation of FIG. 5.
Figure 4B:
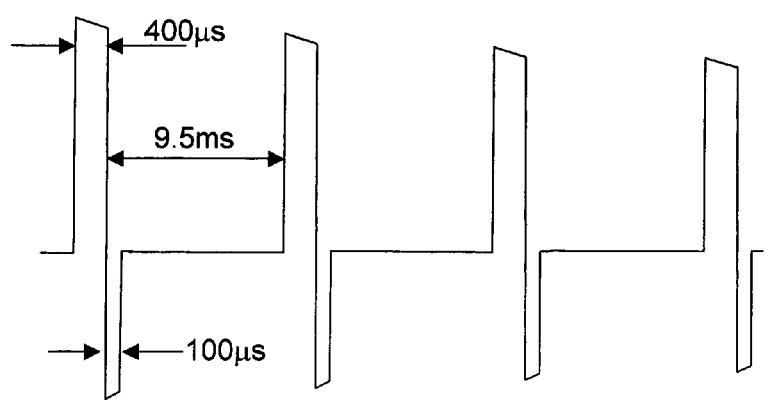

In one implementation, the MPES waveform delivered to the patient is a multiphasic waveform, e.g., as described in U.S. Pat. No. 6,096,063. Referring to FIG. 4a, the waveform is composed of at least one biphasic pulse. The biphasic pulses are approximately 100-200 volts in amplitude and may be concatenated, e.g., into a multiphasic pulse train up to 100 ms in duration, though preferably a series of four 10 ms biphasic pulse for a total of 40 ms. The biphasic pulses may additionally be shortened in duration, thus increasing the frequency content of the MPES waveform. In another embodiment shown in FIG. 4b, the individual biphasic pulses are 500 microseconds in duration, with a 400 microsecond first phase and 100 microsecond second phase with a spacing between pulses of 9.5 ms. It has been found that GLUT4 glucose transport channels respond to these higher frequencies while the longer duration, lower frequency 10-20 ms duration biphasic pulses are more effective at stimulating the myocardial contraction that is necessary for the $Ca^+$ chemo-mechanical pump to function. The pulses are delivered at a rate of 0.1-4 Hz during the course of MPES treatment.

In an additional embodiment, pulses of different characteristics may be interspersed to provide optimal transfer of the therapeutic agents. For instance, the pulse train of FIG. 4a is alternated with that of FIG. 4b either singularly or in groups. The average amplitude of the pulse train can be adjusted by changing the duty cycle of the biphasic pulses. For instance, for shorter duration biphasic pulses, less than approximately 1 ms in duration, the myocardium responds to the average current of the pulse train. Thus, with a 50% duty cycle, there is very little effect on the myocardium. Increasing the duty cycle increases the average current. In some implementations, the capacitor voltage may be charge to an arbitrary value based on the measured impedance of the patient prior to delivery of therapy as well as expected levels of current required for the therapy. During the delivery of the MPES pulses, the average current can be adjusted dynamically by altering the biphasic pulse duty cycle. By adjusting the duty cycle, waveform shape and rate of the pulses, the device can seamlessly adjust the type of therapy delivered to the patient based on the measured underlying condition of the patient.

Figure 5:
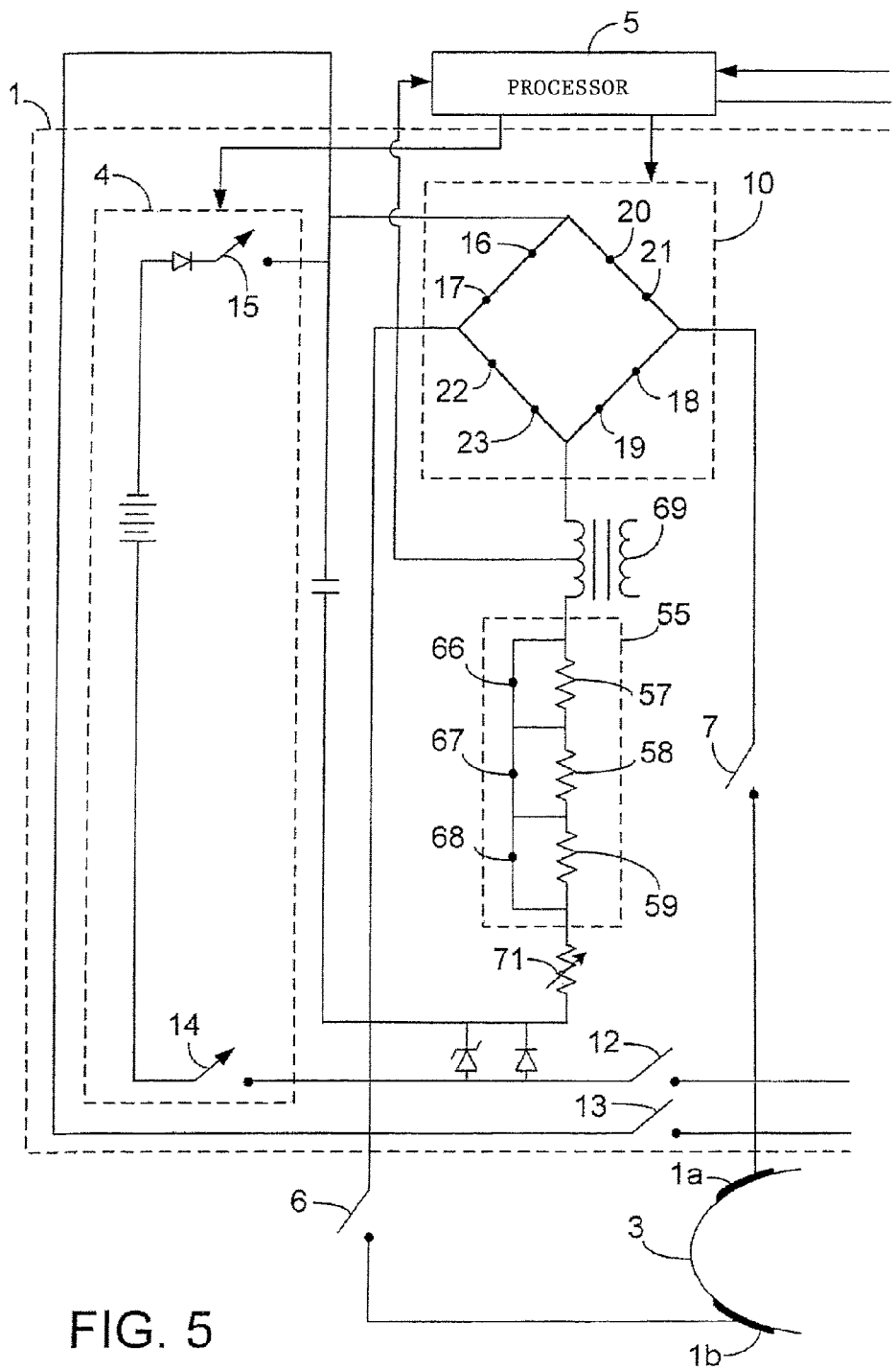
FIG. 5 is a schematic of the circuitry for a biphasic defibrillator implementation.

Referring to FIG. 5,6 the electromagnetic (EM) energy delivery means 1 is comprised of storage capacitor 2 which is charged to a therapeutically effective voltage by a charging circuit 4, under control of the processing means 5, while relays 6, 7 and the H-Bridge 10 are open.

Figure 1:
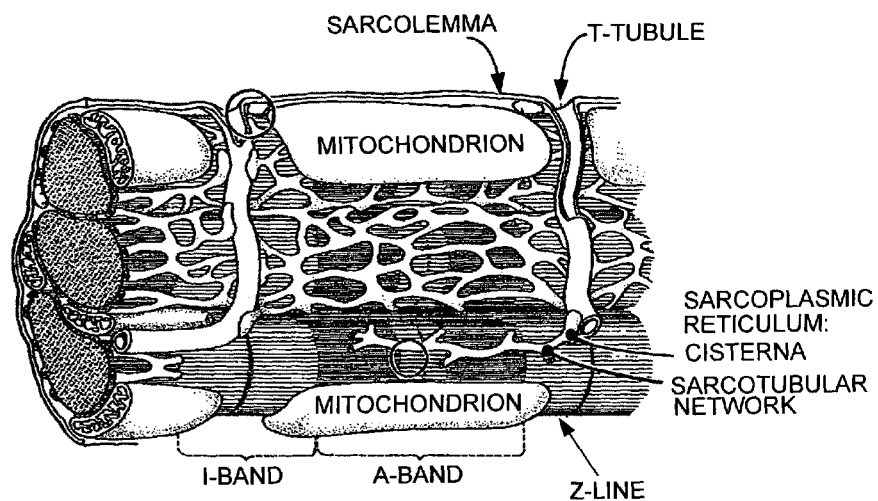
FIG. 1 shows the ultrastructure of the myocardial cell.
Figure 2:
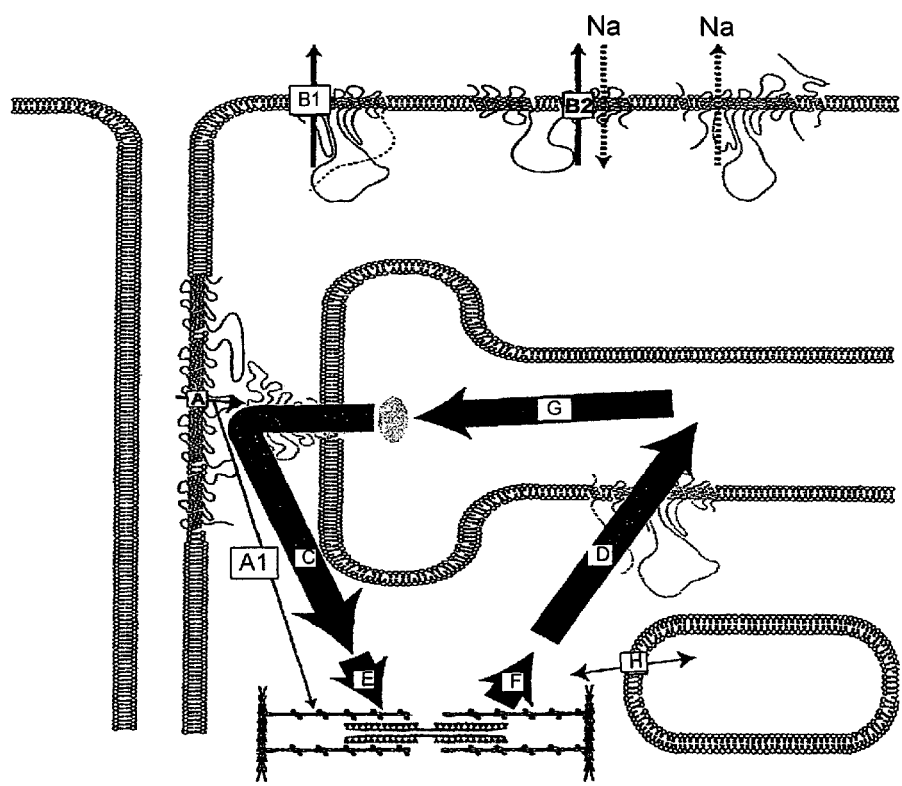
FIG. 2 shows the primary calcium fluxes during systole and diastole.

Upon determination by processing means 5, using any existing methods known to those skilled in the art, of the appropriate time to deliver the defibrillation energy to the patient, relay switches 14 and 15 are opened, and relay switches 6, 7 are closed. Then, the electronic switches 16, 17, 18, and 19 of H-bridge 10 are closed to allow electric current to pass through the patient's body in one direction, after which electronic switches 16, 17, 18, and 19 of H-bridge 10 are opened and 20, 21, 22, and 23 of H-bridge 10 are closed to allow the electric current to pass through the patient's body in the other direction. Relay switches 14 and 15 are combined in double-pole double-throw configuration (DPDT) to reduce size and cost. Electronic switches 16-23 are controlled by signals from respective opto-isolators, which are, in turn, controlled by signals from the processing means 5. As shown in FIG. 2, processing means 5 may be a microprocessor, such as a Hitachi SH-3 40 combined with a read only memory device (ROM) 41, random access memory (RAM) 42, Clock 43, real time clock 44, analog-to-digital 45 and digital-to-analog 46 converters, power supply 47, reset circuit 48, general purpose input/output 49, and user interface in the form of a display 49 and input keys 50 and other circuitry known to those skilled in the art. A measurement means 52 is provided for measurement of electrical, electrocardiographic, physiological or anatomical parameters of the patient, the processing means 5 controlling the waveform parameters of at least one of the discharge pathways based on this measurement. Relay switches 6, 7 which are also controlled by the processing means 5, isolate patient 3 from leakage currents of H-bridge switches 16-23 which may be about 500 microamperes.

Resistive circuit 55 that include series-connected resistors 57, 58, 59 are provided in the current path, each of the resistors being connected in parallel with shorting switch 66-68 controlled by processing means 5. The resistors may be of unequal value and stepped in a binary sequence such that with the various combinations of series resistance values, there are $2^n$ different combinations, where n is the number of resistors. Immediately prior to delivering the therapeutic defibrillation energy a smaller amplitude "sensing" pulse is delivered by closing H-bridge switches 16-19 and the resistor shorting switches 66-68 are all open so that current passes through the resistors in series. The current sensing transformer 69 senses the current that passes through the patient through their respective electrode pairs 1a, 1b, from which the processing means 5 determines the resistance of the patient 3.

The initial sensing pulse is integral with, i.e., immediately followed by, a biphasic defibrillation waveform, and no re-charging of storage capacitor occurs between the initial sensing pulse and the biphasic defibrillation waveform. If the patient resistance sensed during the initial sensing pulse is low, all of the resistor-shorting switches 66-68 are left open at the end of the sensing pulse so that all of the resistors 57-59 remain in the current path (the resistors are then successively shorted out during the positive phase of the biphasic defibrillation waveform in the manner described below in order to approximate a rectilinear positive phase). Thus, the current at the beginning of the positive first phase of the biphasic defibrillation waveform is the same as the current during sensing pulse. If the patient resistance sensed during the sensing pulse is high, some or all of the resistor-shorting switches 66-68 are closed at the end of the sensing pulse, thereby shorting out some or all of the resistors.

Thus, immediately after the sensing pulse, the biphasic defibrillation waveform has an initial discharge current that is controlled by microprocessor 46, based on the patient impedance sensed by current-sensing transformer 69. The current level of the sensing pulse is always at least 50 percent of the current level at the beginning of positive first phase, and the sensing pulse, like the defibrillation pulse, is of course a direct-current pulse.

By appropriately selecting the number of resistors that remain in the current path, the processing means reduces (but does not eliminate) the dependence of peak discharge current on patient impedance, for a given amount of charge stored by the charge storage device. During the positive phase of the biphasic waveform, some or all of the resistors 57-59 that remain in series with the patient 3 are successively shorted out. Every time one of the resistors is shorted out, an upward jump in current occurs in the waveform, thereby resulting in the sawtooth ripple shown in the waveform of FIG. 3. The ripple tends to be greatest at the end of the rectilinear phase because the time constant of decay (RC) is shorter at the end of the phase than at the beginning of the phase. Of course, if all of the resistors have already been shorted out immediately after the end of the sensing pulse, the positive phase of the biphasic waveform simply decays exponentially until the waveform switches to the negative phase.

Figure 7:
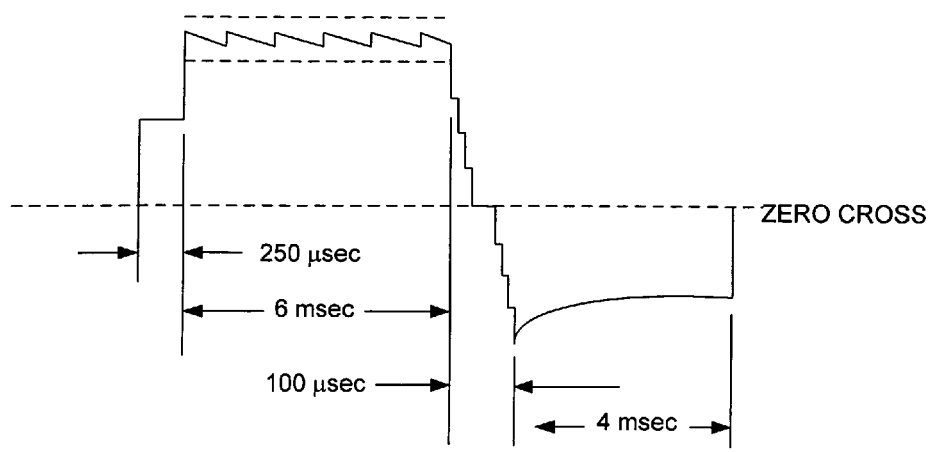
FIG. 7 shows an individual biphasic waveform from FIG. 4a, 4b.
Figure 8:
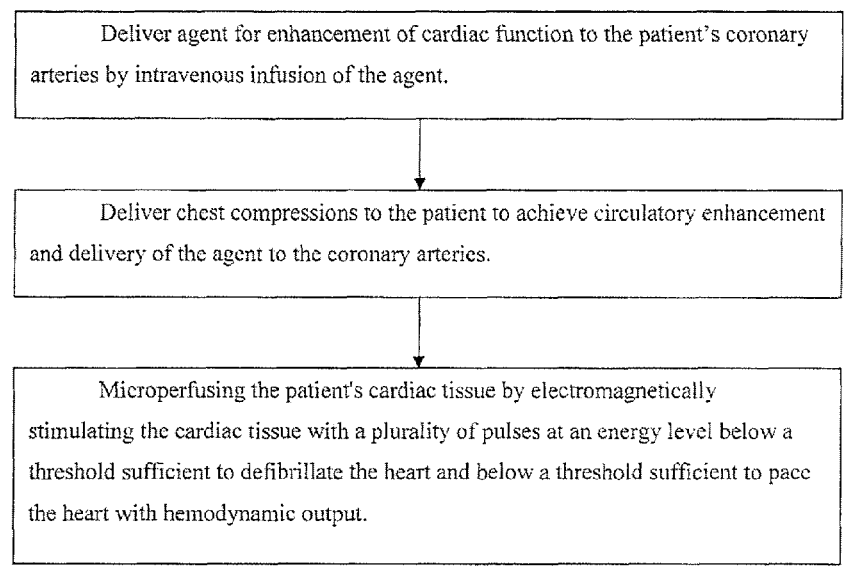
FIG. 8 is a block diagram of another implementation of the method of the invention.
Figure 9:
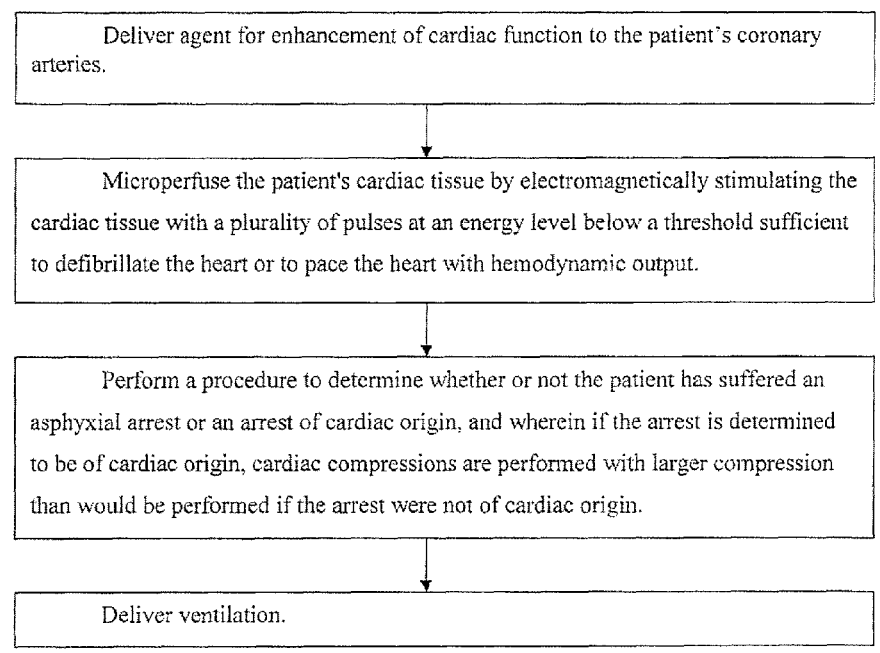
FIG. 9 is a block diagram of another implementation of the method of the invention.

As is shown in FIG. 7, at the end of the positive phase, the current waveform decreases through a series of rapid steps from the end of the positive phase to the beginning of negative phase, one of the steps being at the zero crossing. Processing means 5 accomplishes this by (1) successively increasing the resistance of resistive circuit 55, 56 in fixed increments through manipulation of resistor-shorting switches 57-59, then (2) opening all of the switches in H-bridge 10 to bring the current waveform down to the zero crossing, then (3) reversing the polarity of the current waveform by closing the H-bridge switches that had previously been open in the positive phase of the current waveform, and then (4) successively decreasing the resistance of resistance circuit 55 in fixed increments through manipulation of resistor-shorting switches 66-68 until the resistance of resistance circuit 55 is the same as it at the end of the positive phase.

In one implementation a variable resistor 71 is provided in series with the other resistors 57-59 to reduce the sawtooth ripple. Every time one of the fixed-value resistors 57-59 is shorted out, the resistance of variable resistor 71 automatically jumps to a high value and then decreases until the next fixed-value resistor is shorted out. This tends, to some extent, to smooth out the height of the sawtooth ripple from about 3 amps to about 0.1 to 0.2 amps, and reduces the need for smaller increments of the fixed-value (i.e., it reduces the need for additional fixed-value resistor stages).

Unlike a defibrillation pulse which occurs, at most, at intervals of 0.5-1 minute, the MPES pulses occur at approximately a 1 Hz rate. Charging circuit 4 charges the high voltage capacitor 2 to the required voltage in the intervals between delivery of the MPES pulses.

The electromagnetic stimulation of the MPES waveform may take the form of magnetic stimulation via a electrical coil that receives the current pulse from the high voltage capacitor 2. Magnetic stimulation can provide some additional benefits over electrical stimulation in that the fields are unattenuated at the cytosolic level by the intervening conductive tissues such as blood and skeletal muscle.

Various agents for the enhancement of cardiac function may be delivered in some implementations, including, for example, metabolites and metabolic enhancing agents. The delivery may be performed in a variety of ways, including, for example, intravenous, intraosseus, or transcutaneous infusion. And delivery may include circulatory enhancement to assist in delivery of the agent from the infusion site to the coronary arteries. Circulatory enhancement can be performed in a variety of ways, including, for example, by manual chest compression, by using an automatic chest compression device such as the Autopulse (available from Revivant, San Jose Calif.), or by using a cardiac mechanical pump.

Many other implementations of the invention other than those described above are within the invention, which is defined by the following claims. The invention applies to both defibrillation and cardioversion; in the claims, references to defibrillation should be interpreted as also encompassing cardioversion. Some implementations of the invention do not require defibrillation or cardioversion. The invention applies, in general, to both internal and external defibrillation.

What is claimed is:

1. A method of treating a patient in cardiac arrest (including in fibrillation, electrochemical dissociation, or asystole), the method comprising:
    delivering an agent for enhancement of cardiac function to the patient's coronary arteries, wherein delivering the agent comprises intravenous infusion of the agent and a circulatory enhancement method for delivery of the agent to the coronary arteries; and
    microperfusing the patient's cardiac tissue by electromagnetically stimulating the cardiac tissue with a plurality of microperfusing pulses, applied via electrodes external to the patient, wherein the microperfusing pulses are
    at an energy below a threshold sufficient to defibrillate the patient's heart and below a threshold sufficient to pace the patient's heart with hemodynamic output,
    but of a frequency, duration, and energy level to produce sufficient myocardial cell contraction for pumping of Calcium ions into the cell interior without causing electroporation of the myocardial cells.

2. The method of claim 1 wherein the circulatory enhancement method comprises manual chest compressions.

3. The method of claim 1 wherein the circulatory enhancement method comprises assistance by a cardiac mechanical pump.

4. The method of claim 1 further comprising delivering a defibrillation pulse to the patient's cardiac tissue following the delivering and microperfusing steps.

5. The method of claim 1 wherein the order in which the steps are performed is delivering the agent, followed by circulatory enhancement of the agent, followed by microperfusing.

6. The method of claim 1 further comprising delivering calcium.

7. The method of claim 1 wherein the electromagnetic stimulating comprises applying an electrical current.

8. The method of claim 1 wherein the electromagnetic stimulating comprises applying a magnetic field.

9. The method of claim 1 wherein the delivering step comprises cardiac compression performed by chest compression.

10. The method of claim 1, wherein the metabolic agent comprises a metabolite selected from the group consisting of aspartate, oxidized form of nicotinamide adenine dinucleotide (NAD+), proglycogen, and 2-oxoglutarate.

* * * * *